United States Patent [19]

Willen et al.

[11] Patent Number: 5,779,733
[45] Date of Patent: Jul. 14, 1998

[54] LUMBAR SPINE COMPRESSION DEVICE

[75] Inventors: Jan A. G. Willen, Mölnlycke; Arne Gaulitz, Billdal; Barbro Danielsson, Lindome; Thomas Nicklasson, Onsala, all of Sweden

[73] Assignee: Bohuslandstinget, Sweden

[21] Appl. No.: 591,640

[22] PCT Filed: May 24, 1995

[86] PCT No.: PCT/SE95/00581

§ 371 Date: Jan. 24, 1996

§ 102(e) Date: Jan. 24, 1996

[87] PCT Pub. No.: WO95/31936

PCT Pub. Date: Nov. 30, 1995

[30] Foreign Application Priority Data

Jan. 24, 1994 [SE] Sweden ................... 9401793

[51] Int. Cl.⁶ ........................................ A61F 5/00
[52] U.S. Cl. .............................. 606/237; 606/201
[58] Field of Search ...................... 606/237, 201, 606/203; 128/774, 781; 378/204, 205, 203, 209; 5/621, 623

[56] References Cited

U.S. PATENT DOCUMENTS

| 3,629,581 | 12/1971 | Smith | 378/209 |
| 4,202,355 | 5/1980 | Loeffler . | |
| 4,407,277 | 10/1983 | Ellison | 606/203 |
| 4,580,554 | 4/1986 | Goodley | 606/201 |
| 4,669,106 | 5/1987 | Ammerman | 378/209 |

*Primary Examiner*—Michael Buiz
*Assistant Examiner*—Kevin Truong
*Attorney, Agent, or Firm*—Brumbaugh, Graves, Donohue & Raymond

[57] ABSTRACT

The present invention relates to a device for use in medical procedures for imaging a patient's lumbar spine while in a supine position by computerized tomography and magnetic resonance tomography, comprising a garment-like structure such as waistcoat substantially surrounding a portion of the body of a patient, a foot plate having pressure sensors and being attached to a substantially stationary surface, a pulling cord attached to said waistcoat and said foot plate as well as a transmission attached to said pulling cord and said foot plate for exerting a pressure on the spine.

10 Claims, 1 Drawing Sheet

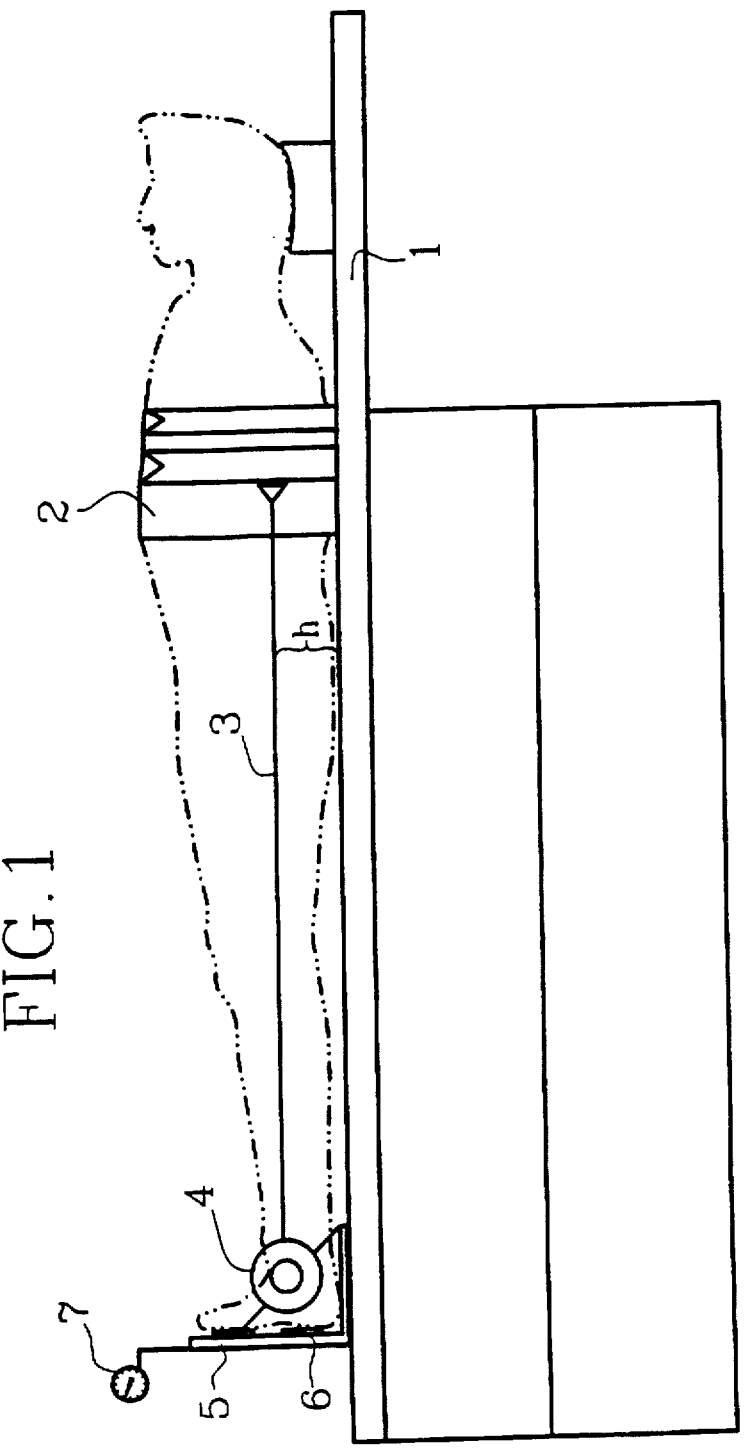
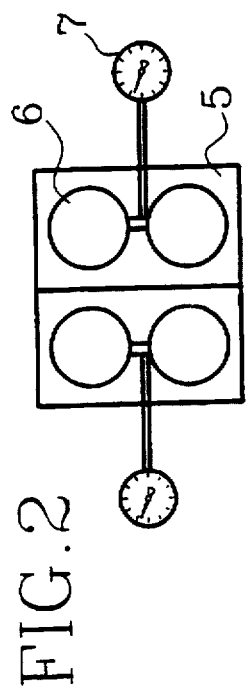
FIG. 1
FIG. 2

LUMBAR SPINE COMPRESSION DEVICE

CROSS-REFERENCE TO RELATED APPLICATIONS

This application is a national stage application of International Application No. PCT/SE95/00581, filed May 24, 1995, and claims foreign priority benefits under 35 U.S.C. §119 of Sweden Application No. 9401793-6, filed May 24, 1994.

BACKGROUND OF THE INVENTION

1. Field of the Invention

The present invention relates to a device for diagnostic purposes to be used in examination of the lumbar spine by computerized tomography and magnetic resonance tomography.

The object of the present invention is to provide a device, the use of which aids in the adequate and reproducible examination of the lumbar spine in connection with computerized tomography and/or magnetic resonance tomography, in particular for the diagnosis of stenoses of the spinal cord canal and nerve structures (spinal stenosis) present therein.

2. Description of the Prior Art

Traditionally, the patient is examined using computerized tomography and magnetic resonance tomography in a relaxed supine position, which means that those structures in connection with the spinal cord canal, which are variable (intervertebral disks, ligaments, and small joints), are subject to minimal load. At load, the pressure in, inter alia, the intervertebral disks increases, resulting in a protuberance, which in turn diminishes the space in the spinal cord canal and nerve and vessel structures present therein. Upon examination of the spinal cord canal of the lumbar spine while suspecting spinal stenosis, and using computerized tomography or magnetic resonance tomography, there is a need for being able to load the lumbar spine in the same way as it occurs when standing upright, simultaneously as the patient is placed in a horizontal position.

Prior art patent U.S. Pat. No. 3,629,581 teaches a device for positioning a patient's shoulders in connection with an X-ray examination of the spine, whereby the upper spinal column is pressed down towards the examination table and thereby makes it possible to obtain a good X-ray picture of the upper vertebrae. In that case a pressure is applied to the spinal column of the patient while lying down via two flexible strings provided with handles for the patient, which strings are arranged around a foot plate.

U.S. Pat. No. 4,534,076 relates to a device for placing a patient in an upside down position in order to deload a patient's spinal column.

There is thus a problem to be solved for the examination of the spinal canal of the lumbar spine.

BRIEF DESCRIPTION OF THE DRAWINGS

FIG. 1 shows a lateral view of one embodiment of a device according to the present invention.

FIG. 2 shows one embodiment of a foot plate of the device according to FIG. 1.

DETAILED DESCRIPTION OF THE INVENTION

It has now surprisingly been shown possible to be able to solve this problem by the present invention which is characterized in that it comprises a garment-like structure such as a waistcoat arranged to be placed around the body of a patient, a foot plate comprising pressure sensors attached to a resting surface, pulling cords arranged between said waistcoat and said foot plate as well as a transmission attached to said pulling cords.

By means of the present invention a controlled load of the lumbar spine can be obtained when the waistcoat is applied around a patient's body and is drawn, using a predetermined force, against said foot plate by means of said pulling/transmission, against which foot plate the patient's feet are positioned, whereby the pressure sensors indicate the pressure/pulling obtained, and thereby the compression of the lumbar spine as desired.

By means of the compression obtained, the space in the spinal canal is reduced and the diagnosis of the spinal stenosis is facilitated and become more safe.

The invention will now be described in detail with reference to the attached drawing, showing a preferred device of the invention, whereby FIG. 1 shows a lateral view of one embodiment of a device according to the present invention, and FIG. 2 shows one embodiment of a foot plate of the device according FIG. 1.

The present invention comprises a resting surface 1 for of a patient suitable for being used with a device for computerized tomography or magnetic resonance tomography. The computerized tomography and the magnetic resonance tomography are well known diagnostic units and are not the subject of the present invention and will thus not be described in greater detail. It further comprises a waistcoat 2, which is arranged to be placed around the upper body of a patient e.g., the thoracic region, whereby it is fastened suitably using cords of the burdock type. The waistcoat 2 is applied firmly, but still comfortably. Pulling cords 3 run on each side of the patient from the waistcoat 2, whereby said cords are placed at a height "h" above the resting surface. This height will be more closely defined later. The pulling cords 3 are attached at their other ends to a transmission 4, of which a simple embodiment is a mechanical rolling device, manually or motor driven. The transmission 4 is in turn attached to a foot plate 5, which has a dimension that accommodate the two feet of a patient when place upon it. The foot plate 5 is provided with pressure sensors 6 in the form of air cylinders which are further connected to a respective manometer 7 for each foot. The pressure sensors 6 registers the pressure of each foot on the foot plate 5 and the respective pressure can be read on the nanometers 7.

The height "h" which the pulling cords 3 are arranged above the resting surface 1, can be varied depending on the build of the patient but also depending on the desired load on the spinal column/lumbar spine.

The pressure sensors 6 may also be connected to a motor which affects the pulling of the pulling cords 3, whereby a predetermined, adjusted value can be maintained as the pressure sensors 6 control this motor.

Further, the pressure sensors 6 can be arranged to control a pressure cylinder arranged between the pulling cords 3 and the foot plate 5, which pressure cylinder acts as the transmission.

During an examination a patient is placed on his back upon the resting surface 1, the waistcoat 2 is arranged around the thorax of the patient and the pulling cords 3 are connected to the waistcoat 2. The pulling cords 3 are then pulled by means of the transmission 4, either manually or by means of a motor, whereby they are pulled to a predetermined value, most often depending on the weight of the patient, whereby for the average patient this value shall provide a load of about 40 kg on the lumbar spine, i.e. about half the body weight, which is the normal load at upright standing. The pressure sensors 6 determine the pressure and which can be read on the manometers, to show whether the load is reached, if it is evenly distributed, etc.

The patient is then introduced into the computerized tomography or magnetic resonance tomography equipment in order to obtain the desired pictures of the desired region.

We claim:

1. A device for use in medical complementary examination for imaging a patient's spine while in a supine position, comprising a flexible garment-like structure which contacts and substantially surrounds a portion of the patient's body, a foot plate having a transmission mechanism connected thereto for exerting a compression pressure on the spine and at least one pressure sensor connected said foot plate, and wherein at least a portion of said foot plate being secured to a substantially stationary surface, and at least one pulling cord mechanism connecting said garment-like structure to said transmission.

2. A device according to claim 1, wherein the medical complementary examination for imaging is computerized tomography and magnetic resonance tomography.

3. A device according to claim 1, wherein the garment-like structure is in the form of a waistcoat which along with the foot plate is attached to a surface upon which the patient rests.

4. A device according to claim 1, wherein the transmission is a roller and attached pulling cord mechanism.

5. A device according to claim 1, wherein the transmission is at least one pressure cylinder and attached pulling cord mechanism.

6. A device according to claim 1, further comprising at least one pressure sensor connected to the transmission.

7. A device according to claim 1, wherein the transmission is activated by means of a motor.

8. A device according to claim 3, wherein the distance between the pulling cord mechanism and the surface upon which the patient rests may be varied by changing the location at which the pulling cord mechanism is attached to the garment-like structure and transmission.

9. A device according to claim 1, wherein the foot plate comprises pressure sensors.

10. A device according to claim 1, wherein the pressure sensor is a tension sensor connected to the foot plate.

* * * * *